United States Patent [19]
Mansell et al.

[11] Patent Number: 5,282,601
[45] Date of Patent: Feb. 1, 1994

[54] ISOLATION SYSTEM FOR MEDICAL IMAGING EQUIPMENT

[75] Inventors: Scott T. Mansell, Waterford; Paitoon Nimityongskul, Mukwonago, both of Wis.

[73] Assignee: General Electric Company, Milwaukee, Wis.

[21] Appl. No.: 717,961

[22] Filed: Jun. 20, 1991

[51] Int. Cl.$^5$ ............................................. F16M 11/00
[52] U.S. Cl. .................... 248/638; 248/636; 248/562
[58] Field of Search ............. 248/638, 560, 562, 581, 248/605, 606, 611, 613, 619, 620, 621, 631, 636, 614

[56] References Cited

U.S. PATENT DOCUMENTS

| | | | |
|---|---|---|---|
| 1,243,358 | 10/1917 | Stoddard | 248/620 X |
| 1,834,907 | 12/1931 | Tortt. | |
| 2,912,212 | 11/1959 | Lowe et al. | 248/621 X |
| 3,141,523 | 7/1964 | Dickie. | |
| 3,836,134 | 9/1974 | Lowe et al. | |
| 4,520,987 | 6/1985 | Eguchi et al. | |
| 4,553,231 | 11/1985 | D'Alayer de Costemore. | |
| 4,560,136 | 12/1985 | Basore. | |
| 4,711,135 | 12/1987 | Horiuchi et al. | |
| 4,858,879 | 8/1989 | Miyamoto et al. | 248/636 X |

FOREIGN PATENT DOCUMENTS

| | | | |
|---|---|---|---|
| 320467 | 5/1957 | Switzerland | 248/614 |
| 524461 | 8/1940 | United Kingdom | 248/611 |

*Primary Examiner*—Alvin C. Chin-Shue
*Attorney, Agent, or Firm*—Quarles & Brady

[57] ABSTRACT

The shock isolation system for CT equipment or the like employs a C-support holding isolation unit on either side of a support plate for the CT machine. Each isolation unit is made up of an elastomeric tube capped by a diaphragm and enclosing an air-tight volume. Different spring constants are produced by the isolation unit depending on whether only the diaphragm or the entire tube is compressed, allowing effective vibration isolation and shock protection for the supported equipment. The elastomeric tube provides both axial and lateral isolation eliminating the need for isolation units along multiple axes.

1 Claim, 3 Drawing Sheets

ISOLATION SYSTEM FOR MEDICAL IMAGING EQUIPMENT

BACKGROUND OF THE INVENTION

This invention relates to a vibration and shock isolation system for use with medical imaging equipment, and in particular, to a system suitable for protecting such equipment from damage in mobile military applications.

In medical computed tomography (CT), a cross-sectional image of a patient is generated by computer processed data collected by a CT machine. The CT machine employs an x-ray source collimated so as to form a fan beam of x-rays. The fan beam is directed through the patient along a fan beam plane generally parallel to the cross section of the image to be produced. A series of detectors, positioned within the fan beam plane, receive the radiation after it passes through the patient and provide a series of intensity measurements along a number of rays from the x-ray source to each detector element. After one such projection is obtained, the x-ray source and detector are rotated about the patient to a new position and a new projection is taken. Multiple projections taken at different angles form a projection set which may be "reconstructed" into the tomographic image. The patient is normally supported on a radiolucent table which extends through the fan beam plane and which may be moved to a variety of positions within the fan beam plane.

The x-ray source and x-ray detectors are mounted on a gantry for rotation about the patient to obtain the projection set as described above. The rotating gantry may also hold an x-ray tube cooling system and certain detector electronics and thus may have considerable mass. The gantry is mounted to a rigid support frame constructed to hold the gantry precisely within a single plane and thus to ensure the integrity of the projection set data.

The entire CT machine, including the table but excluding the remote console used for controlling the CT machine and for receiving and displaying the tomographic images, may weigh on the order of 2.5 tons. Nevertheless, the CT machine is a sensitive instrument which must be protected from shocks and vibration. The mathematics of image reconstruction requires that the x-ray tube and detectors be precisely aligned during the rotation of the gantry to avoid imaging artifacts, i.e., errors in the reconstructed image visible as obscuring rings or streaks. Accordingly, care must be taken that the gantry runs true without deviation or wobble.

Large shocks may distort the gantry or its supports and may damage electronic subcomponents such as the x-ray tube. Lower amplitude but continuous vibrations may cause misalignment of the x-ray tube and the detectors, so as to reduce the image quality, or may cause premature failure of the CT system's numerous electronic components. Some form of mechanical isolation is critical for a CT system that is not in a fixed site in a stable environment.

While the physics of shock protection and vibration isolation are generally understood, the isolation of a CT machine represents a considerable challenge because of both its large mass and its sensitive construction. Adapting a CT machine for use in a military environment or the like, to be transported in areas having only unimproved or damaged roads, requires a high degree vibration isolation and protection against impulse shocks. For example, in a military mobile hospital, the CT machine may be routinely subject to 12" drops.

It may be expected that the primary shocks to the CT system during transportation will be directed along a vertical axis; however, this cannot be guaranteed. Conventional techniques for cushioning a load against vertical and rotational shocks may require complex arrangements of multiple shock absorbing elements positioned along different axis and both adding to the complexity of the isolation system and reducing its reliability.

Ultimately, the complex nature of the interaction between the CT structure and the shock isolation system under a variety of shocks requires that the isolation system be fine tuned to particular CT system and shelter being used. Such tuning is difficult with typical metal spring isolators.

SUMMARY OF THE INVENTION

The present invention provides a simple means of shock isolating large sensitive equipment such as a CT machine.

Specifically, the CT system is mounted on a rigid support plate. A C-support holds, between its opposed faces, a first and second isolator on either side of the support plate. The isolators employ an elastomeric tube defining an air-tight volume, the axis of the elastomeric tube directed between the faces of the C-support.

It is one object of the invention to produce an isolation system having isolation units disposed only along a single axis that provides isolation from vertical shocks, as well as from transverse or lateral shocks. The clamping of the two isolation units between the parallel faces of the C-support provides resistance against motions that would tend to move the support plate in a lateral direction.

It is a further object of the invention to provide isolation not only for a primary shock but also for a rebound occurring after that primary shock. The opposed isolators ensure that at least one isolator will be in a preferred state of compression rather than elongation during the shock and its rebound.

The isolators may be compressed along the axis of the elastomeric tube and the elastomeric tube may be closed on one end by a elastomeric diaphragm having an outwardly extending boss.

It is another object of the invention to isolate the CT system not only from low amplitude vibration but also to prevent destructive forces resulting from higher amplitude shocks. The lower amplitude vibrations compress the boss toward the elastic tube by a slight amount and produce a spring constant dependent primarily on flexure of the diaphragm alone. Larger shocks press the boss below the wall of the elastomeric tube deforming the tube and producing a higher spring constant commensurate with protection of the CT equipment from shocks. A non-compressible spacer ring may be fitted around the boss to adjust the amount of compression required before tube's walls are deformed and the the higher spring constant is produced.

It is another object of the invention to provide a system for isolating heavy and delicate equipment that will permit adjustment of the dynamics of the isolation and its height once the equipment is in place. This adjustment is provided by the use of the spacer ring and by controlling the air pressure within the isolator.

The foregoing and other objects and advantages of the invention will appear from the following description. In the description reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DESCRIPTION OF THE PREFERRED EMBODIMENT

Figure 1:
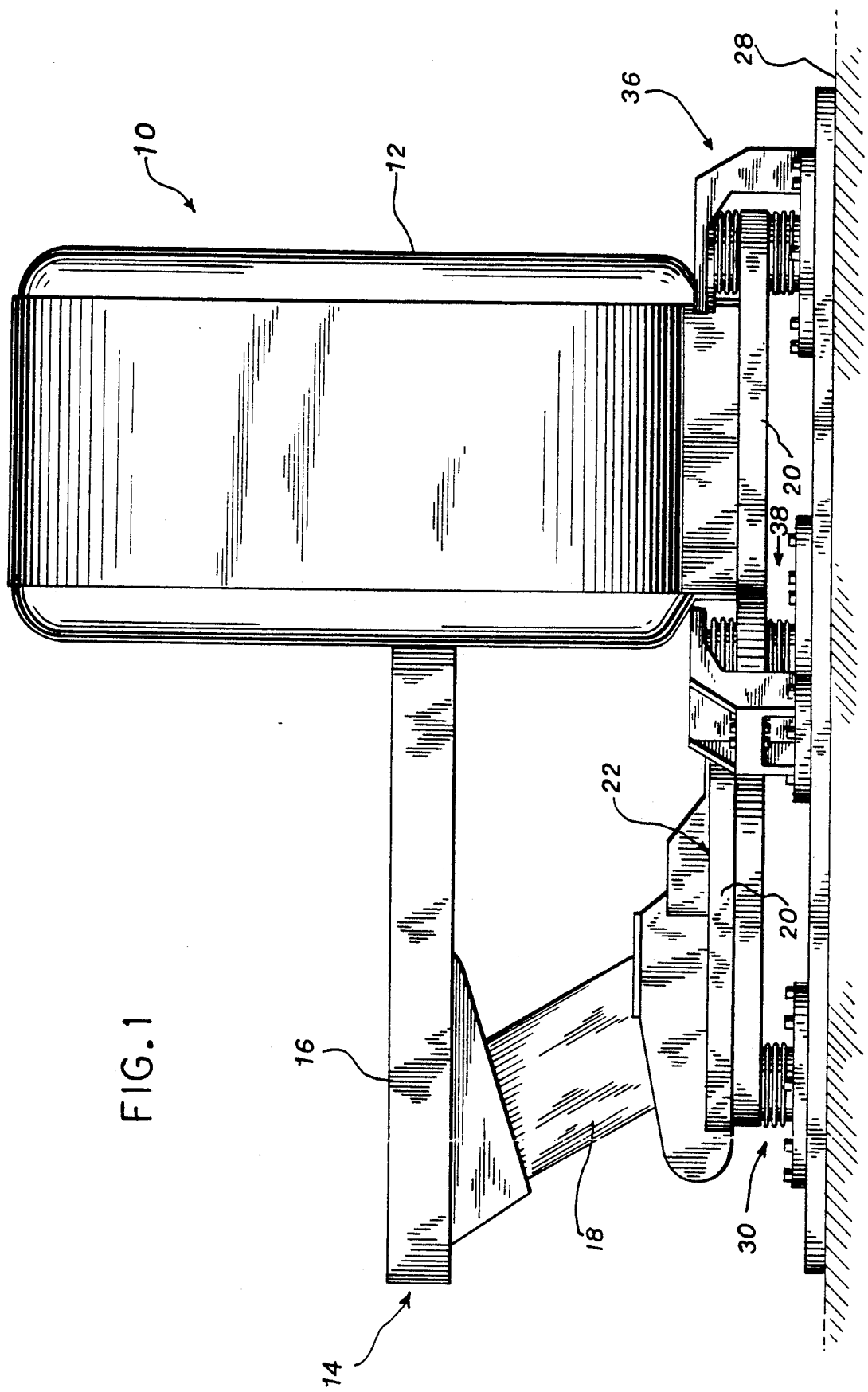
FIG. 1 is a view in elevation of a CT machine showing the support platform holding the gantry unit and the patient table and showing the position of the isolation units with respect to the support platform.

Referring to FIG. 1, a CT system 10 comprises generally a toroidal gantry unit 12, housing a rotating gantry holding an x-ray tube and x-ray detectors (not shown), and a table unit 14. The table unit 14 includes an elongate table surface 16, for supporting a supine patient (not shown) and a table pedestal 18 for supporting a table surface 16 with respect to the gantry unit 12 and for moving the table surface 16 into and out of the toroid of the gantry unit 12 during a CT scan. A gantry unit 12 may weigh on the order of 1716 pounds, while a table unit 14 will be substantially lighter on the order of 539 pounds.

Figure 2:
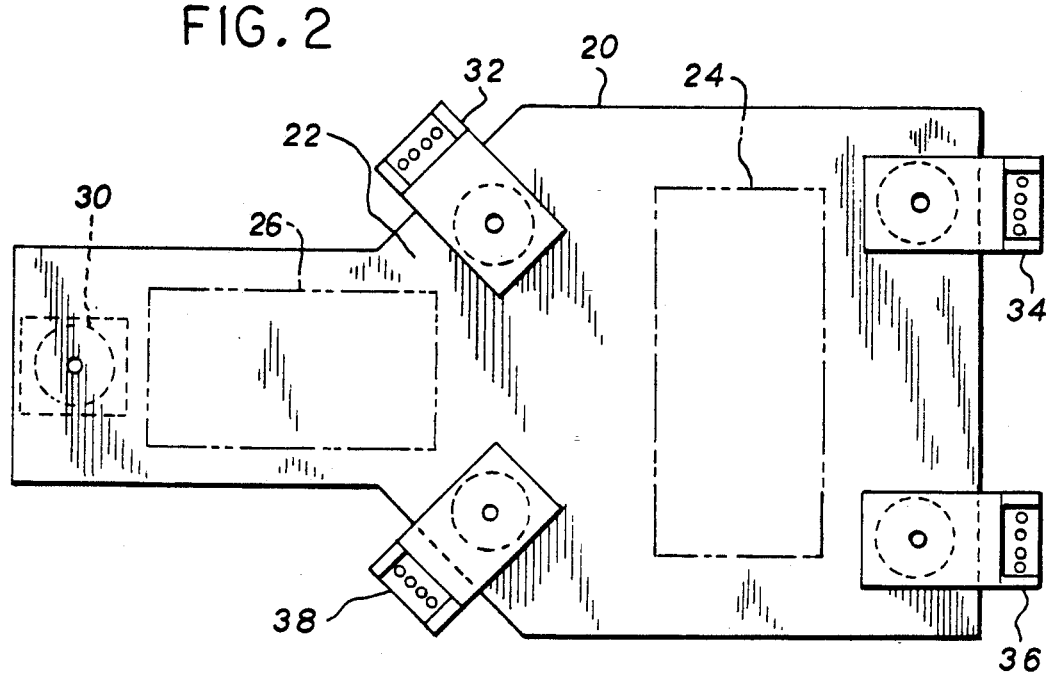
FIG. 2 is a plan view of the support platform of FIG. 1 also showing the locations of the support units.

Referring also to FIG. 2, the gantry unit 12 and table unit 16 are mounted on a support plate ,20 which presents a substantially rigid and horizontal planar upper surface 22. The support plate 22 receives the gantry unit 12, over a generally rectangular area 24 of the upper planar surface 22 and the table pedestal 18, over a generally rectangular area 26 of the upper planar surface 22, both positioned as they would be on a floor in a conventional installation, as will be understood to those of ordinary skill in the art.

The support plate 20 is preferably constructed of a welded network of tubular struts (not shown) sandwiched between upper and lower sheets of steel, the sheets which form the upper planar surface 22 and a lower planar surface 21. The combination of the tubular network and laminating steel sheets produces a lightweight and relatively inflexible structure.

The support plate 20 is held about its periphery away from a shelter floor 28, by five isolation units 30-38. Four of these isolation units, 32, 34, 36 and 38, are spaced approximately evenly around area 24 so as to center the mass of the gantry unit 12 among them. Three of the isolation units, 32, 38 and 30, are spaced approximately evenly around area 24, so as to center the mass of the table unit 14 among them.

Figure 3:
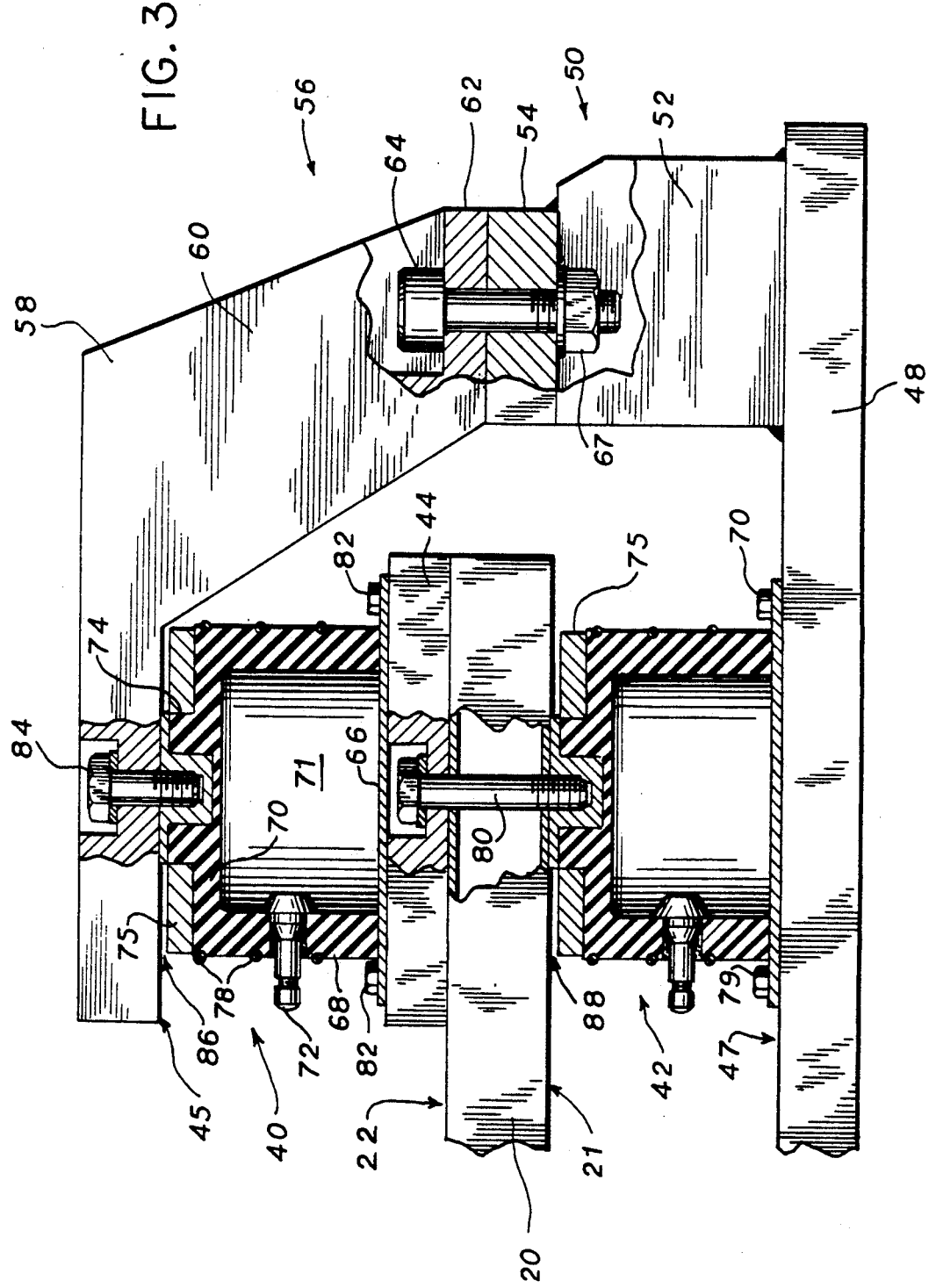
FIG. 3 is a view in elevation and partial cross-section of the isolation units of FIG. 1 in position on the support plate.

Referring to FIGS. 1 and 3, each isolation unit, except for isolation unit 30, holds an edge of the support plate 20 cushioned between an upper and lower air spring isolator 40 and 42. Specifically, for each of these isolation units, the upper surface 22 of the support plate 20 holds a spacer plate 44 and the upper surface of the spacer plate 44 contacts the lower surface of the first air spring isolator 40. Conversely, the lower surface 21 of the support plate 20 contacts the upper surface of the lower air spring isolator 42. The upper surface of the upper air spring isolator 40 and the lower surface of the lower spring mount 42 abut, respectively, opposing upper and lower faces 45 and 47 of a C-support 46 which holds the upper and lower air spring isolators 40 and 42 in place about the support plate 20.

The C-support 46 is constructed of a weight dispersion plate 48 which is attached to the floor of the shelter 28 by a series of bolts (not shown) running through the shelter floor 28, and forms the lower face 47 of the C-support 46. The shelter floor 28 may be composed of a honeycomb structure unable to support high point loads and therefore the weight dispersion plate 48 serves to spread the weight carried by each isolation unit 30-38 over a broader surface. At one edge of the weight dispersion plate 48, an upwardly extending bridge 50 is attached having vertically extending risers 52 and a horizontal span portion 54. The span portion 54 presents an upward surface substantially parallel to the upper face 47 of the weight dispersion plate 48 and forms one-half of a spine 56 connecting the two opposing faces 45 and 47 of the C-support 46 in opposition.

An upper channel plate 58 provides the upper face 45 of the C-support 46 and is attached to the upwardly extending bridge 50 by means of a downwardly extending bridge 60, the bridge 60 descending from one edge of the upper channel plate 58 and having a horizontal span portion 62 whose lower face abuts the upper face of span 54. Spans 54 and 62 are held together by means of four cap screws 64 extending through spans 54 and 62 and retained by a Nuts 62, the heads and Nuts 67 of the cap screws 64 compressing the spans 62 and 54 together between them and thus holding the upper channel plate 58 substantially parallel to the weight dispersion plate 54 and the upper opposing face 45 opposite the lower opposing face 47.

Isolation unit 30 differs from the isolation units 32, 34, 36 and 38 by the fact that only a single air spring isolator 42 is employed and is positioned beneath the support plate 20. Thus, for isolation unit 30, the weight dispersion plate 48 does not include an upward bridge 50 but simply has bolted to its upper surface the air spring isolator 42 which in turn supports the lower surface of the support plate 20.

Each air spring isolator 40 and 42 is constructed of a generally rigid plate 66 capping a lower end of a generally cylindrical elastomeric tube 68. The upper end of the elastomeric tube is capped by an elastomeric diaphragm 70, which together with the rigid plate 66, forms a cylindrical air-tight cavity 71 within the elastomeric tube 68. A tire valve 72 passes through one wall of the elastomeric tube 68 to provide a means for admitting or releasing air or other compressible fluids from this cavity 71.

Centered on the upper side of the elastomeric diaphragm 70 is an elastomeric boss 74 which is capped by a threaded plate 76 for receiving a bolt 80 or 84. The threaded plate 76 defines the upper surface of the air spring isolators 40 or 42 and the rigid plate 66 defines the lower surface of the air spring isolators 40 or 42. An aluminum spacer ring 75 is placed around the boss 74 and controls the gap 86 between the upper edge of the elastomeric tube 68 and the upper face 45 of the C-support 46 (for air spring isolator 40) or the gap 88 between the upper edge of the elastomeric tube 68 and the lower face 21 of the support plate 20 (for the air spring isolator 42). This spacing affects the functional relationship between the compression and effective spring constant of the air spring isolators 40 and 42 as will be described below.

A set of steel rings 78 constrain the outer periphery of the elastomeric tube 68 during extreme compression of the air spring isolator 40 or 42. An air spring isolator suitable for use with the present invention is described in detail in U.S. Pat. No. 3,836,134 hereby incorporated by reference.

Each isolation unit 32-38 is assembled by attaching the weight dispersion plate 48 to the floor of the shelter 28 by means of a number of bolts (not shown) passing through the weight dispersion plate 48 and the floor of the shelter 28. The rigid plate 66 of the first air spring isolator 42 is attached to the upper surface 47 of the weight dispersion plate 48 by means of a set of bolts 79. The edge of the support plate 20 holding the CT machine 10 is then placed on top of the affixed air spring isolator 42 and secured by means of a bolt 80 passing through the spacer plate 44, the support 20 and threaded into the threaded plate 76 of air spring isolator 42. Preferably the spacer plate 44 is counterbored to receive the head of the bolt 80 beneath its upper surface.

The rigid plate 66 of the second air spring isolator 40 is then placed on top of the spacer plate 44 and bolted thereto by a series of bolts 82 passing through the rigid plate 66 into the spacer plate 44. The upper channel plate 58 is then attached by means of its bridge 60 to the bridge 50 by means of the cap screws 64 and Nuts 67 as previously described. Once in place, the face 47 of the upper channel plate 58 abuts the upper surface of the threaded plate 76 of the air spring isolator 40 and may be attached thereto by a bolt 84 passing through the upper channel plate 58 and into the threaded plate 76.

The air spring isolators 40 and 42 operate both to isolate the CT system 10 from low amplitude vibrations and to protect the CT system 10 from large shocks. During the isolation of CT system 10 from vibration, the air spring isolators 40 and 42 operate as part of a tuned mass-spring system to provide a mechanical "low pass" filter tuned to prevent movement of the CT system 10 with expected vibrations of the shelter floor 28. The elimination of such vibration serves to prevent fatigue or dislocation of a variety of CT system components including the electronics and the x-Ray tube and the detector array. Such vibrations are distinguished from shocks primarily by their low amplitude and continuous nature and involve a relative movement between the C-support 46 and the support plate 20 of magnitude less than the gap 86 or 88 between the spacer ring 75 and its opposing surface. Accordingly, the flexure of the air spring isolators 40 and 42 during vibration isolation is primarily that of the diaphragm 70 working against the pressure of the air contained within the chamber 71.

During large shocks to the shelter floor 28 the air spring isolators 40 and 42 serve to protect the CT system 10 from damaging impulse forces. Under these circumstances, the air spring isolators 40 and 42 do not isolate the support plate 20 from movement but to move the support plate 20 within acceptable force limits to prevent larger impact forces which would result from the support plate 20 striking of the relatively inelastic surfaces of the C-support 46. During large amplitude shocks, the gaps 86 and 88 are closed by flexure of the upper diaphragm 70 moving the elastomeric boss 74 below the spacer ring 75 and coupling the upper face 45 of the C-support 46 or the lower surface 21 of the support plate 20 directly to the walls of the elastomeric tube 68 which provide a relatively stiffer spring constant and serve to accelerate the support plate 20 so as to prevent the substantially higher forces that would result from a bottoming out of the air spring isolators 40 and 42. Air spring isolators 40 and 42 bottom out when the diaphragm 70 strikes the rigid plate 66.

Figure 4:
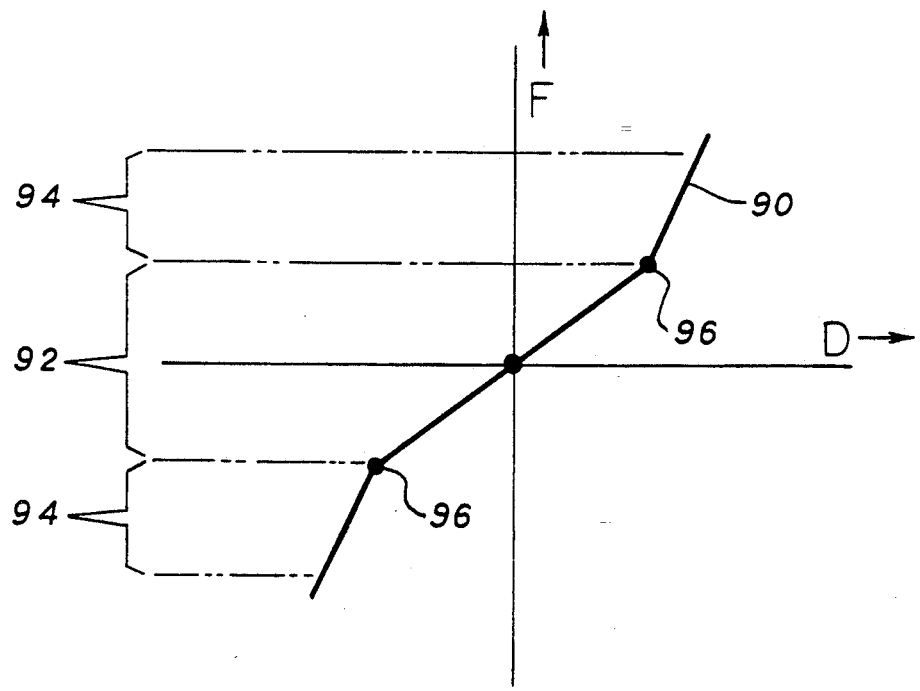
FIG. 4 is a graph showing the forces acting on the CT machine as a function of the displacement of the support plate with respect to the isolation unit of FIG. 1.

Referring to FIG. 4, the present system offers a bi-directional elastic support for the support plate 20 where deflection of the support plate 20 in either direction with respect to the C-support 46 encounters a restoring force. Further, the present invention provides two levels of spring constant, i.e. restoring force, as indicated by the slope of line 90 in FIG. 4 which is relatively lower for small amplitude deviations 92 commensurate with vibration and larger for high amplitude deviations 94 commensurate with shocks. The break points 96 between these two spring constants may be controlled by the size of the spacer plate 75 and hence the size of the gaps 86 and 88, and thus may be tailored to the weight and size of the CT system 10 and the expected environment in which it will operate. It is important to note that a restoring force is exerted both for downward deflection of the support plate 20 and for upward deflection which may be caused by "rebound" after an initial upward shock on the shelter floor 28. It is believed that the rebound may be as damaging as the initial shock. The use of two air spring isolators 40 and 42 permit one air spring isolator to be operated in compression at all times regardless of the direction of the deviation.

The air pressure in each air spring isolator 40 and 42, as controlled by the air introduced through valve 72, provides, to the first order, an offset force in each air spring isolator which is cancelled in the opposed configuration of the present invention. To a second order, the air pressure controls the stiffness of the air spring isolator and thus allow the response of the isolation system to be fine tuned once the CT system 10 is in place on the isolation units 30-38.

A further advantage of the use of the air spring isolators 40 and 42, as described, is that they provide considerable resistance to lateral deflection and for vibration isolation can have approximately the same characteristics laterally as they do vertically. As is generally understood in the art, the relative lateral and vertical stiffness is controlled generally by the height to diameter of the elastomeric tube 68, the durometer value and thickness of the material of the elastomeric tube 68 and the air pressure within the cavity 71. Accordingly, vibration isolation may be accomplished in multiple dimensions through the use of as few as two air spring isolators 40 and 42 on each isolation unit 30-38.

Many modifications and variations of the preferred embodiment which will still be within the spirit and scope of the invention will be apparent to those with ordinary skill in the art. For example, the number of shock isolation units and their location may be changed to address different mass distributions of the CT machine or other medical imaging devices. In order to apprise the public of the various embodiments that may fall within the scope of the invention, the following claims are made.

We claim:

1. An isolation system for a mobile medical imaging system supported on a support plate comprising:

a C-support having first and second inwardly facing surfaces for positioning the support plate therebetween;

a first and second isolator each having outwardly opposed surfaces and each for fitting respectively above and below the support plate and between the first and second inwardly facing surfaces of the C-support, each isolator having one face abutting the support plate and one face abutting the respective first and second inwardly facing surface of the C-support;

wherein the isolator comprises an elastomeric tube defining an air-tight volume incorporating a compressible fluid, the axis of the elastomeric tube being substantially normal to the inwardly facing surfaces of the C-support;

wherein the isolator may be compressed along the axis of the elastomeric tube and wherein a first end of the elastomeric tube is closed by an elastomeric diaphragm having an outwardly extending boss forming one outwardly opposing surface and spaced a first distance away from the first end of the elastomeric tube when the isolator is uncompressed and spaced a second distance less than the first distance away from the first end of the elastomeric tube when the isolator is compressed; and including a non-compressible spacer ring fitting around the boss determining the second distance.

* * * * *